(12) United States Patent
Vincent et al.

(10) Patent No.: US 8,877,996 B2
(45) Date of Patent: Nov. 4, 2014

(54) ALKYLATED AROMATICS PRODUCTION

(71) Applicants: ExxonMobil Chemical Patents Inc., Baytown, TX (US); Technip Process Technology, Inc., Houston, TX (US)

(72) Inventors: Matthew J. Vincent, Kingwood, TX (US); Vijay Nanda, Houston, TX (US); Maruti Bhandarkar, Kingwood, TX (US); Brian Maerz, Chelmsford, MA (US); Terry E. Helton, Bethlehem, PA (US)

(73) Assignees: ExxonMobil Chemical Patents Inc., Houston, TX (US); Technip Process Technology, Inc., Houston, TX (US)

( * ) Notice: Subject to any disclaimer, the term of this patent is extended or adjusted under 35 U.S.C. 154(b) by 0 days.

(21) Appl. No.: 14/075,218

(22) Filed: Nov. 8, 2013

(65) Prior Publication Data

US 2014/0135548 A1 May 15, 2014

Related U.S. Application Data (60) Division of application No. 12/721,326, filed on Mar. 10, 2010, now Pat. No. 8,629,311, which is a continuation of application No. PCT/US2010/026844, filed on Mar. 10, 2010.

(51) Int. Cl.
- *C07C 2/66* (2006.01)
- *C07C 6/12* (2006.01)
- *C07C 7/13* (2006.01)

(52) U.S. Cl.
CPC ... *C07C 2/66* (2013.01); *C07C 7/13* (2013.01); *C07C 6/126* (2013.01); *C07C 2529/08* (2013.01); *C07C 2529/18* (2013.01); *C07C 2529/70* (2013.01)
USPC .......... 585/449; 585/448; 585/467; 585/323; 585/475

(58) Field of Classification Search
CPC ............ C07C 2/66; C07C 6/126; C07C 7/13; C07C 15/073; C07C 15/085
USPC .................... 585/449, 448, 467, 323, 475
See application file for complete search history.

(56) References Cited

U.S. PATENT DOCUMENTS

| | | | |
|---|---|---|---|
| 3,293,192 A | 12/1966 | Maher et al. | |
| 3,308,069 A | 3/1967 | Wadlinger et al. | |
| 3,442,795 A | 5/1969 | Kerr et al. | |
| 3,449,070 A | 6/1969 | McDaniel et al. | |
| 3,524,820 A | 8/1970 | Hemminger | |
| 3,702,886 A | 11/1972 | Argauer et al. | |
| 3,709,979 A | 1/1973 | Chu | |
| 3,766,093 A | 10/1973 | Chu | |
| 3,832,449 A | 8/1974 | Rosinski et al. | |
| RE28,341 E | 2/1975 | Wadlinger et al. | |
| 3,894,104 A | 7/1975 | Chang et al. | |
| 3,923,636 A | 12/1975 | Mead et al. | |
| 3,972,983 A | 8/1976 | Ciric | |
| 4,016,218 A | 4/1977 | Haag et al. | |
| 4,016,245 A | 4/1977 | Plank et al. | |
| 4,076,842 A | 2/1978 | Plank et al. | |
| RE29,948 E | 3/1979 | Dwyer et al. | |
| 4,234,231 A | 11/1980 | Yan | |
| 4,358,362 A | 11/1982 | Smith et al. | |
| 4,401,556 A | 8/1983 | Bezman et al. | |
| 4,439,409 A | 3/1984 | Puppe et al. | |
| 4,556,477 A | 12/1985 | Dwyer | |
| 4,826,667 A | 5/1989 | Zones et al. | |
| 4,954,325 A | 9/1990 | Rubin et al. | |
| 5,030,786 A | 7/1991 | Shamshoum et al. | |
| 5,236,575 A | 8/1993 | Bennett et al. | |
| 5,250,277 A | 10/1993 | Kresge et al. | |
| 5,362,697 A | 11/1994 | Fung et al. | |
| 5,744,686 A | 4/1998 | Gajda | |
| 6,077,498 A | 6/2000 | Diaz Cabanas et al. | |
| 6,231,751 B1 | 5/2001 | Canos et al. | |
| 6,297,417 B1 | 10/2001 | Samson et al. | |
| 6,313,362 B1 | 11/2001 | Green et al. | |
| 6,355,851 B1 | 3/2002 | Wu et al. | |
| 6,617,482 B1 | 9/2003 | Venkat et al. | |
| 6,756,030 B1 | 6/2004 | Rohde et al. | |
| 6,894,201 B1 | 5/2005 | Schmidt et al. | |
| 6,995,295 B2 | 2/2006 | Clark et al. | |
| 7,199,275 B2 | 4/2007 | Smith | |
| 7,652,184 B2 | 1/2010 | Clark | |
| 2007/0179329 A1 | 8/2007 | Clark | |

FOREIGN PATENT DOCUMENTS

| | | |
|---|---|---|
| EP | 0 293 032 | 11/1988 |
| WO | WO 2009/017881 | 2/2009 |

*Primary Examiner* — Thuan D Dang (57) ABSTRACT

Disclosed is a process for the production of alkylated aromatics by contacting a feed stream comprising an alkylatable aromatic, an alkylating agent and trace amounts of water and impurities in the presence of a first catalyst and an alkylation catalyst wherein such water and impurities are removed in order to improve the cycle length of such alkylation catalysts. Water and at least a portion of impurities are removed in a dehydration zone. A reaction zone having a first catalyst which, in some embodiments is a large pore molecular sieve, acts to remove another portion of impurities, such as nitrogenous and other species. An alkylation zone having an alkylation catalyst which, in some embodiments is a medium pore molecular sieve or a MCM-22 family material, acts to remove additional impurities, and to alkylate the alkylatable aromatic compound.

20 Claims, 8 Drawing Sheets

ALKYLATED AROMATICS PRODUCTION

CROSS REFERENCE TO RELATED APPLICATION

This application is a divisional of U.S. application Ser. No. 12/721,326, filed Mar. 10, 2010, now U.S. Pat. No. 8,629,311, which claims priority to International Application Serial No. PCT/US2010/026844, filed Mar. 10, 2010, the disclosure of which is incorporated herein by reference in their entireties.

FIELD

The present disclosure relates to a process for the production of alkylated aromatic compounds from a feed stream comprising an alkylating agent, an alkylatable aromatic and trace amounts of water and impurities.

BACKGROUND

Alkylated aromatic compounds, such as cumene, ethylbenzene and sec-butyl benzene, are often produced by the liquid phase alkylation reaction of alkylatable aromatics (e.g., benzene) and alkylating agents (e.g., olefins such as ethylene, propylene and butylene) in the presence of acidic molecular sieve catalysts (e.g., zeolites). Liquid phase aromatics alkylation processes often result in reduced operating costs and fewer undesirable byproducts produced (e.g., xylenes) than in earlier vapor phase technologies.

Acidic molecular sieve catalysts that may be used for such liquid phase aromatic alkylation reactions include zeolite beta, zeolite Y, zeolite omega, ZSM-5, ZSM-12, MCM-22, MCM-36, MCM-49, MCM-56, MCM-58, MCM-68, UZM-8, faujasite, Mordenite, porous crystalline magnesium silicates and Tungstate-modified zirconia (e.g., $Zr(WO_4)_2$, all of which are known in the art.

Operation of liquid phase aromatics alkylation reactions especially at relatively low temperatures has resulted in greater catalyst sensitivity to trace impurities (e.g., "catalyst poisons") in the alkylatable aromatic or alkylating agent feed streams. Such impurities often result in more frequent catalyst regeneration requirements and reduced ultimate life of the catalyst before replacement is necessary. Catalyst replacement often involves a process shutdown, lost production and significant costs. A variety of processes have been developed for pretreating aromatic and/or alkylating agent feed streams to remove catalyst poisons. These processes include distillation, adsorption and extraction.

U.S. Pat. No. 6,313,362 (Green) teaches an aromatic alkylation process in which the alkylation product is contacted with a large pore molecular sieve catalyst such as MCM-22 in a liquid phase step to remove impurities prior to liquid phase alkylation. Impurities taught as being removed include olefins, diolefins, styrene, oxygenated organic compounds, sulfur-containing compounds, nitrogen-containing compounds and oligomeric compounds.

U.S. Pat. No. 4,358,362 (Smith) teaches a method for enhancing catalytic activity of a zeolite catalyst by contacting a feed stream which contains a catalytically deleterious impurity with a zeolitic sorbent. This disclosure uses a sorbent with a Si/Al ratio greater than 12, 10-12-membered rings, and a Constraint Index between 1 and 12, preferably ZSM-11.

U.S. Pat. No. 5,030,786 (Shamshoum) teaches a process for production of ethylbenzene in which the catalyst lifetime is increased by reducing the concentration of water in the feed to the reactor.

U.S. Pat. No. 5,744,686 (Gajda) teaches a process for the removal of nitrogen compounds from an aromatic hydrocarbon stream by contacting the stream with a selective adsorbent having an average pore size less than about 5.5 Angstroms. The selective adsorbent is a non-acidic molecular sieve selected from the group consisting of pore closed zeolite 4A, zeolite 4A, zeolite 5A, silicalite, F-silicalite, ZSM-5 and mixtures thereof.

A process for preparing alkylated benzenes is taught in U.S. Pat. No. 6,297,417 (Samson). The process includes contacting a benzene feedstock with a solid acid, such as acidic clay or acidic zeolite, in a pretreatment zone at a temperature between about 130° C. and about 300° C. to improve the lifetime of the alkylation and transalkylation catalyst.

U.S. Pat. No. 6,355,851 (Wu) teaches a zeolite-catalyzed cumene synthesis process in which benzene feedstock is contacted with a "hot" clay bed, followed by distillation of the benzene feedstock to separate the benzene from the higher molecular weight materials formed from olefinic poisons during the hot clay treatment, followed by a "cold" clay treatment wherein the benzene distillate is contacted with an ambient-temperature clay. The propylene feedstock is pretreated by contact with an alumina to remove trace sodium compounds and moisture, a molecular sieve to remove water and two modified aluminas to remove other catalyst poisons. The pretreated propylene and benzene feedstocks are then reacted in the presence of a zeolite catalyst to form cumene without causing rapid degradation of the catalyst's activity.

PCT published application WO0214240 (Venkat) teaches removal of polar contaminants in an aromatic feedstock by contacting it with molecular sieves with pore size greater than 5.6 Angstroms at temperatures below 130° C.

U.S. Pat. No. 6,894,201 (Schmidt) teaches removing nitrogen compounds from an alkylation substrate such as benzene prior to alkylation using a conventional adsorbent bed which adsorbs basic organic nitrogen compounds and a hot adsorbent bed of acidic molecular sieve which adsorbs weakly basic nitrogen compounds such as nitrites. Schmidt teaches that water facilitates the adsorption of the weakly basic nitrogen compounds and that running an alkylation substrate stream from a fractionation column of elevated temperature and suitable water concentration to the hot adsorbent bed may be advantageous.

U.S. Pat. No. 7,199,275 (Smith) teaches a process for hydrocarbon conversion in which a partially dehydrated hydrocarbon feedstock is contacted with at least two different molecular sieve materials, including a first molecular sieve having a Si/Al molar ratio of less than about 5 and a second molecular sieve having a Si/Al molar ratio of greater than about 5. Also, Smith teaches processes in which such feedstocks are contacted with a first molecular sieve having pores of at least about 6 Angstroms and a second molecular sieve having pores of less than about 6 Angstroms.

These prior references do not provide for the alkylation of a feed stream by contact with an alkylation catalyst, wherein the feed stream contains an alkylatable aromatic compound, an alkylating agent and trace amounts of water and impurities and a portion of the water and impurities are removed at the same time as the feed stream is alkylated. The presence of water and impurities in the feed stream negatively impact the catalytic activity and cycle length of the alkylation catalyst in alkylation processes.

Therefore, there is a need for an improved process for the production of alkylated aromatics by contacting such a feed stream with a first and then a different second alkylation catalyst to remove a portion of water and impurities and alkylate a portion of the alkylatable aromatic such that the adverse impact on the activity and cycle length on such alkylation catalyst by water and impurities is mitigated. This disclosure meets this and other needs.

SUMMARY OF THE DISCLOSURE

The present disclosure describes a process for the production of alkylated aromatic compounds from a feed stream comprising an alkylating agent, an alkylatable aromatic and trace amounts of water and impurities in the presence of a first catalyst and an alkylation catalyst wherein such water and impurities are removed in order to improve the cycle length of the alkylation catalyst. Water, and at least a portion of impurities, are removed in a dehydration zone. In a non-reactive guard bed, the dehydrated stream is contacted with a first catalyst in a reaction zone wherein another portion of impurities are removed. An alkylation zone having an alkylation catalyst acts to remove additional impurities, and to alkylate the alkylatable aromatic compound with an alkylating agent by contact with the alkylation catalyst.

The first catalyst in the reaction zone in some embodiments is a large pore molecular sieve. The alkylation catalyst in the alkylation zone in some embodiments is a medium pore molecular sieve or a MCM-22 family material.

While not intending to be bound by any theory, it is believed that the dehydration step reduces the concentration of water and optionally reduces the level of impurities in the alkylatable aromatic feed. A portion of the impurities are removed at the same time as a portion of the water. This enables the first alkylation step to remove a portion, preferably a major portion, of the remaining impurities, such as nitrogenous and other species, contained in the alkylatable aromatic feed, and to alkylate a portion of the alkylatable aromatic compound. Preferably at least 80%, at least 70% or at least 60% by weight, of the remaining impurities are removed. The second alkylation step in turn acts to remove a portion of the remaining impurities, and to alkylate a major portion of the alkylatable aromatic compound. Preferably at least 80%, at least 70% or at least 60% by weight, of the alkylatable aromatic compound is alkylated with an alkylating agent.

The alkylated aromatic compounds produced comprise primarily mono-alkylated aromatic compounds with trace amounts of poly-alkylated aromatic compounds produced concomitantly in the alkylation reaction zones. The poly-alkylated aromatic compounds may then be converted to additional mono-alkylated compounds by contact with additional alkylatable aromatic compounds in the presence of a separate transalkylation catalyst in a transalkylation step.

DETAILED DESCRIPTION OF THE PREFERRED EMBODIMENTS

Definitions

The term "alkylatable aromatic compound" as used herein means an aromatic compound that may receive an alkyl group. One non-limiting example of an alkylatable aromatic compound is benzene.

The term "alkylating agent" as used herein means a compound which may donate an alkyl group to an alkylatable aromatic compound. Non-limiting examples of an alkylating agent are ethylene, propylene and butylene. Another non-limiting example is any poly-alkylated aromatic compound that is capable of donating an alkyl group to an alkylatable aromatic compound.

The term "aromatic" as used herein in reference to the alkylatable aromatic compounds which are useful herein is to be understood in accordance with its art-recognized scope which includes substituted and unsubstituted mono- and polynuclear compounds. Compounds of an aromatic character which possess a heteroatom (e.g., N or S) are also useful provided they do not act as catalyst poisons, as defined below, under the reaction conditions selected.

The term "at least partially liquid phase" as used herein means a mixture having at least 1 wt. % liquid phase, optionally at least 5 wt. % liquid phase, at a given temperature, pressure and composition.

The term "catalyst poison" as used herein means an impurity, defined herein, which acts to reduce the cycle-length of a molecular sieve or zeolite.

The term "cycle length" as used herein means the total on-oil time between regenerations, or the on-oil time period between fresh load and regeneration. After the fresh catalyst or the regenerated catalyst being brought on-oil, the catalyst may be deactivated due to coke deposition or poison. As the catalyst becomes deactivated, the reaction zone has to be operated at higher temperatures to maintain the same productivity or catalytic activity. The catalyst has to be regenerated once the reaction zone temperature reaches a threshold temperature, typically determined by metallurgy of the reactor or when economic factors warrant.

The term "framework type" is used herein has the meaning described in the "Atlas of Zeolite Framework Types," by Ch. Baerlocher, W. M. Meier and D. H. Olson (Elsevier, 5th Ed., 2001.)

The numbering scheme for the elements of the Periodic Table Groups as used herein has the meaning described in the Periodic Table of Elements as published by International Union of Pure and Applied Chemistry on 22 Jun. 2007.

The term "impurities" as used herein includes, but is not limited to, compounds having at least one of the following elements: nitrogen, halogens, oxygen, sulfur, arsenic, selenium, tellurium, phosphorus and Group 1 through Group 12 metals.

The impurities content as used in this disclosure means the wppm of impurities based on the total weight of the combined alkylatable aromatic compound and alkylating agent in the reaction zone.

The term "MCM-22 family material" (or "material of the MCM-22 family" or "molecular sieve of the MCM-22 family"), as used herein, includes:

(i) molecular sieves made from a common first degree crystalline building block "unit cell having the MWW framework topology." A unit cell is a spatial arrangement of atoms which is tiled in three-dimensional space to describe the crystal as described in the "Atlas of Zeolite Framework Types," by Ch. Baerlocher, W. M. Meier and D. H. Olson (Elsevier, 5th Ed., 2001.);

(ii) molecular sieves made from a common second degree building block, a 2-dimensional tiling of such MWW framework type unit cells, forming a "monolayer of one unit cell thickness," preferably one c-unit cell thickness;

(iii) molecular sieves made from common second degree building blocks, "layers of one or more than one unit cell thickness", wherein the layer of more than one unit cell thickness is made from stacking, packing, or binding at least two monolayers of one unit cell thick of unit cells having the MWW framework topology. The stacking of such second degree building blocks can be in a regular fashion, an irregular fashion, a random fashion and any combination thereof; or (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system.

The term "mono-alkylated aromatic compound" means an aromatic compound that has only one alkyl substituent. Non-limiting examples of mono-alkylated aromatic compounds are ethylbenzene, iso-propylbenzene (cumene) and sec-butylbenzene.

The term "on-oil" as used herein is to be understood as the time the catalyst is being brought under alkylation or transalkylation conditions. The alkylation or transalkylation conditions include temperature, pressure, alkylatable aromatic compound(s), alkylating agent(s) and WHSV, which are suitable to covert at least 1 wt. %, preferably at least 10 wt. % of the alkylatable aromatic compound(s) (based on the total alkylatable aromatic compound(s) in the feed) to the mono-alkylated aromatic compound(s).

The term "poison capacity" as used herein means the millimoles of collidine (a catalyst poison) absorbed per gram of a catalyst sample that is dried under nitrogen flow at 200° C. for 60 minutes on a Thermogravametric Analyzer (Model Q5000, manufactured by TA Instruments, New Castle, Del.). After drying, the collidine catalyst poison is sparged over the catalyst sample for 60 minutes at a collidine partial pressure of 3 torr. The poison capacity is calculated from the following formula: (Catalyst Sample Weight after Sparging with collidine−Dried Catalyst Sample Weight)×$10^6$÷(Molecular Weight of Collidine×Dried Catalyst Sample Weight). When the Catalyst Sample Weight and the Dried Catalyst Sample Weight is measured in grams, the molecular weight of collidine is 121.2 grams per millimole.

The term "poly-alkylated aromatic compound" as used herein means an aromatic compound that has more than one alkyl substituent. A non-limiting example of a poly-alkylated aromatic compound is poly-alkylated benzene, e.g., di-ethylbenzene, tri-ethylbenzene, di-isopropylbenzene and tri-isopropylbenzene.

The term "wppb" as used herein is defined as parts per billion by weight.

The term "wppm" as used herein is defined as parts per million by weight.

Feedstocks and Products

Suitable unsubstituted aromatic compounds that may be used for this disclosure include benzene, naphthalene, anthracene, naphthacene, perylene, coronene and phenanthrene, with benzene being preferred.

Substituted aromatic compounds which may be used for the disclosure should possess at least one hydrogen atom directly bonded to the aromatic nucleus. The aromatic rings may be substituted with one or more alkyl, aryl, alkaryl, alkoxy, aryloxy, cycloalkyl, halide and/or other groups which do not interfere with the alkylation reaction. Generally the alkyl groups which can be present as substituents on the aromatic compound contain from 1 to about 22 carbon atoms and usually from about 1 to 8 carbon atoms, and most usually from about 1 to 4 carbon atoms.

Suitable substituted aromatic compounds that may be used for this disclosure include, but are not limited to, toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, iso-hexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene.

Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include, but are not limited to, hexylbenzene, nonylbenzene, dodecylbenzene, pentadecylbenzene, hexyltoluene, nonyltoluene, dodecyltoluene, pentadecytoluene and the like. Very often alkylate is obtained as a high boiling fraction in which the alkyl group attached to the aromatic nucleus varies in size from about $C_6$ to about $C_{16}$.

Reformate streams that may contain substantial quantities of benzene, toluene and/or xylene may be particularly suitable as an alkylatable aromatic feed for the process of this disclosure. Although the process is particularly directed to the production of ethylbenzene from polymer grade and dilute ethylene, it is equally applicable to the production of other $C_7$-$C_{20}$ alkylaromatic compounds, such as cumene, as well as $C_{6+}$ alkylaromatics, such as $C_8$-$C_{16}$ linear and near linear alkylbenzenes.

Suitable alkylating agent(s) that may be used in this disclosure comprise alkene compound(s), alcohol compound(s) and/or alkylbenzene(s) and mixtures thereof. Other suitable alkylating agents that may be useful in the process of this disclosure generally include, but are not limited to, any aliphatic or aromatic organic compound having one or more available alkylating aliphatic groups capable of reaction with the alkylatable aromatic compound. Examples of suitable alkylating agents are $C_2$-$C_{16}$ olefins, such as $C_2$-$C_5$ olefins, including ethylene, propylene, the butenes and the pentenes; $C_1$-$C_{12}$ alkanols (inclusive of monoalcohols, dialcohols, trialcohols, etc.), preferably $C_1$-$C_5$ alkanols, such as methanol, ethanol, the propanols, the butanols and the pentanols; $C_2$-$C_{20}$ ethers, e.g., $C_2$-$C_5$ ethers including dimethylether and diethylether; aldehydes such as formaldehyde, acetaldehyde, propionaldehyde, butyraldehyde and n-valeraldehyde; and alkyl halides such as methyl chloride, ethyl chloride, the propyl chlorides, the butyl chlorides and the pentyl chlorides, polyalkylated aromatic compound(s), e.g., bi-alkylated benzenes (e.g., bi-ethylbenzene(s) or bi-isopropylbenzenes) and tri-alkylated benzene(s) (e.g., tri-ethylbenzenes or tri-isopropylbenzenes), and so forth. Thus the alkylating agent may preferably be selected from the group consisting of $C_2$-$C_5$ olefins, $C_1$-$C_5$ alkanols, bi-ethylbenzene(s), bi-isopropylbenzene(s), tri-ethylbenzene(s) and/or tri-isopropylbenzene(s).

Impurities

In this disclosure, the feed stream comprising the alkylatable aromatic compound may comprise impurities. Optionally, the first alkylating agent stream and/or the second alkylating agent stream may comprise impurities. The impurities comprise a compound having at least one of the following elements: nitrogen, halogens, oxygen, sulfur, arsenic, selenium, tellurium, phosphorus and Group 1 through Group 12 metals. Examples of such impurities include collidine and N-formyl morpholine. For the purposes of this disclosure, the term "impurities" does not include water, $H_2O$.

In some embodiments, the amount of said impurities in said feed stream (or the first and/or the second alkylating agent stream) is less than 20 wppm, less than 15 wppm, less than 10 wppm, less than 5 wppm or less than 1 wppm based on the weight of said feed stream.

Water Content

In one or more embodiments, the feed stream may comprise water. Optionally, the first alkylating agent stream and/or the second alkylating agent stream may comprise water. The feed stream or the alkylating agent stream(s) may be dehydrated by distillation, adsorption, evaporation, extraction or flashing, for example, in one or more dehydration zones. The dehydration zone may be a distillation column, a benzene column or a flashing column, lights column or an extractor, absorber or flash drum.

In some embodiments, the feed stream is saturated with water at the temperature and pressure conditions of the feed stream. In other embodiments, the amount of water in said feed stream is at least 500 wppm, at least 400 wppm, at least 300 wppm or at least 200 wppm based on the weight of said feed stream.

The level of impurities or water may be measured by conventional techniques, such as, GC, GC/MS, or other suitable techniques known to one skilled in the art.

Reaction Conditions

The disclosed process includes: (1) a dehydration zone operated under suitable dehydration conditions to remove at least a portion of water and optionally, a portion of the impurities; (2) a first alkylation reaction zone having a first alkylation catalyst, wherein the first alkylation zone is operated under suitable first reaction conditions to remove a major portion of remaining impurities and to alkylate a portion of the alkylatable aromatic compound; and (3) a second alkylation reaction zone having a second alkylation catalyst which is different from the first alkylation catalyst, wherein the second alkylation zone is operated under suitable second reaction conditions to remove a portion of remaining impurities and alkylate a major portion of the alkylatable aromatic to produce an additional amount of mono-alkylated aromatic compounds.

In the dehydration zone, the suitable dehydration conditions are conventional dehydration conditions known in the art to separate water and impurities from an aromatic stream.

In the first alkylation reaction zone and/or second alkylation reaction zone, when an alkylatable aromatic compound and an alkylating agent are contacted under conditions of at least partially liquid phase, suitable first and second conditions, respectively, include a temperature of 100 to 285° C., preferably, a temperature from 150 to 260° C.; a pressure of 689 to 4601 kPa-a, preferably, a pressure of 1500 to 3000 kPa-a; and a WHSV based on both alkylating agent and alkylatable aromatics for the overall reactor of 10 to 100 $hr^{-1}$, preferably, 20 to 50 $hr^{-1}$. The overall molar ratio of the alkylatable aromatic compound to the alkylating agent (e.g., benzene and ethylene, respectively) ranges from 1:1 to 10:1, 2:1 to 8:1, 3:1 to 7:1, or 1.5:1 to 4.5:1.

In some embodiments, the first alkylation reaction zone may be operated as a reactive guard bed in which at least a portion of impurities in the feed stream are removed. In this embodiment, the overall molar ratio of the alkylatable aromatic compound to the alkylating agent (e.g., benzene and ethylene, respectfully) is much higher than in alkylation service alone, in the range from 10:1 to 200:1, or 15:1 to 150:1, or 20:1 to 100:1 or 25:1 to 50:1.

In other embodiments, the first reaction alkylation zone is a first reaction zone operated as a non-reactive guard bed in which at least a portion of impurities in the feed stream are removed. In this embodiment, only the alkylatable aromatic compound is fed to the first reaction zone.

In some embodiments, the disclosed process includes a treatment zone having a treatment material, wherein the treatment zone is operated under suitable treatment conditions to remove a portion of impurities. The treatment zone may be upstream or downstream of the dehydration zone. The treatment zone is upstream of the first and second alkylation zones.

When a treatment material is used to remove a portion of impurities, suitable treatment conditions include a temperature from about 30 to 200° C., and preferably between about 60 to 150° C., a weight hourly space velocity (WHSV) of from about 0.1 $hr^{-1}$ and about 200 $hr^{-1}$, preferably from about 0.5 $hr^{-1}$ to about 100 $hr^{-1}$, and more preferably from about 1.0 $hr^{-1}$ to about 50 $hr^{-1}$; and a pressure between about ambient and 3000 kPa-a.

In some embodiments, the disclosed process includes a transalkylation zone operated under suitable transalkylation conditions to produce additional amounts of mono-alkylated aromatic compounds from poly-alkylated aromatic compounds and the alkylatable aromatic compound.

In the transalkylation zone, when poly-alkylated aromatic compounds (e.g., polyethylbenzene(s) or polyisopropylbenzene(s) are contacted with alkylatable aromatic compound under at least partially liquid phase conditions, suitable transalkylation conditions may include a temperature of from about 100 to about 300° C., a pressure of 696 to 4137 kPa-a (101 to 600 psia), a WHSV based on the weight of the polyalkylated aromatic compound(s) feed to the alkylation reaction zone of from about 0.5 $hr^{-1}$ to about 100 $hr^{-1}$ and a molar ratio of benzene to polyalkylated aromatic compound(s) of from 1:1 to 30:1, preferably, 1:1 to 10:1, more preferably, 1:1 to 5:1.

Catalysts

The disclosed process includes: (1) a first alkylation catalyst; and (2) a second alkylation catalyst that is different from the first alkylation catalyst.

The first alkylation catalyst comprises a large pore molecular sieve having a Constraint Index of less than 2 and a first poison capacity.

The Constraint Index is a convenient measure of the extent to which an aluminosilicate or molecular sieve provides controlled access to molecules of varying sizes to its internal structure. For example, aluminosilicates which provide a highly restricted access to and egress from its internal structure have a high value for the Constraint Index, and aluminosilicates of this kind usually have pores of small size, e.g. less than 5 Angstroms. On the other hand, aluminosilicates which provide relatively free access to the internal aluminosilicate structure have a low value for the constraint index, and usually pores of large size. The method by which Constraint Index may be determined is described fully in U.S. Pat. No. 4,016,218.

Suitable large pore molecular sieves include zeolite beta, zeolite Y, Ultrastable Y (USY), Dealuminized Y (Deal Y), Ultrahydrophobic Y (UHP-Y), Rare earth exchanged Y (REY), mordenite, TEA-mordenite, ZSM-3, ZSM-4, ZSM-14, ZSM-18 and ZSM-20. Zeolite ZSM-14 is described in U.S. Pat. No. 3,923,636. Zeolite ZSM-20 is described in U.S. Pat. No. 3,972,983. Zeolite beta is described in U.S. Pat. No.

3,308,069 and U.S. Reissue Pat. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Ultrahydrophobic Y (UHP-Y) is described in U.S. Pat. No. 4,401,556. Rare earth exchanged Y (REY) is described in U.S. Pat. No. 3,524,820. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766,093 and 3,894,104.

The zeolitic materials designated by the International Zeolite Association Structure Committee (IZA-SC) as being of the MWW topology are multi-layered materials which have two pore systems arising from the presence of both 10 and 12 membered rings. The Atlas of Zeolite Framework Types currently classes at least five differently named materials as having this same topology include, but are not limited to MCM-22, ERB-1, ITQ-1, PSH-3 and SSZ-25.

In some embodiments, the second alkylation catalyst, preferably an acidic catalyst comprises a MCM-22 family molecular sieve having a second poison capacity. The MCM-22 family molecular sieves have been found to be useful in a variety of hydrocarbon conversion processes. Examples of MCM-22 family molecular sieve are MCM-22, MCM-36, MCM-49, MCM-56, ITQ-1, ITQ-2, ITQ-30, PSH-3, SSZ-25, ERB-1 and UZM-8.

Materials which belong to the MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), MCM-56 (described in U.S. Pat. No. 5,362,697) and UZM-8 (described in U.S. Pat. No. 6,756,030).

It is to be appreciated that the MCM-22 family molecular sieves described above are distinguished from conventional large pore zeolite alkylation catalysts, discussed below, such as mordenite, in that the MCM-22 materials have 12-ring surface pockets which do not communicate with the 10-ring internal pore system of the molecular sieve.

Alternatively, the second alkylation catalyst, preferably an acidic catalyst, may comprise a medium pore molecular sieve having a Constraint Index of 2-12 (as defined in U.S. Pat. No. 4,016,218), including ZSM-5, ZSM-11, ZSM-12, ZSM-22, ZSM-23, ZSM-35 and ZSM-48. ZSM-5 is described in detail in U.S. Pat. No. 3,702,886 and U.S. Pat. Reissue No. 29,948. ZSM-11 is described in detail in U.S. Pat. No. 3,709,979. ZSM-12 is described in U.S. Pat. No. 3,832,449. ZSM-22 is described in U.S. Pat. No. 4,556,477. ZSM-23 is described in U.S. Pat. No. 4,076,842. ZSM-35 is described in U.S. Pat. No. 4,016,245. ZSM-48 is more particularly described in U.S. Pat. No. 4,234,231.

In one or more embodiments, said first poison capacity of said first alkylation catalyst is greater than said second poison capacity of said second alkylation catalyst, said poison capacity measured by collidine capacity.

In some embodiments, the disclosed process includes a treatment material. The treatment material is selected from the group consisting of clay, resin, Linde type X, Linde type A and combinations thereof. The treatment material may be acidic or non-acidic.

In some embodiments, the disclosed process includes a transalkylation catalyst. The transalkylation catalyst comprises a large pore molecular sieve having a Constraint Index of less than 2. The transalkylation catalyst may be the same as or different from the first alkylation catalyst.

Detail Description of the Process

In operation of one embodiment (e.g., reactive guard bed), the process for producing alkylated aromatic compounds, for example mono-alkylated and poly-alkylated aromatic compounds, such process comprises the steps of: (a) supplying a feed stream to a dehydration zone, said feed stream comprising an alkylatable aromatic compound, water and impurities, wherein said impurities comprise a compound having at least one of the following elements: nitrogen, halogens, oxygen, sulfur, arsenic, selenium, tellurium, phosphorus, and Group 1 through Group 12 metals; (b) removing at least a portion of said water from said feed stream in said dehydration zone to produce a dehydrated stream comprising said alkylatable aromatic compound, any remaining water, and said impurities; (c) contacting at least a portion of said dehydrated stream and a first alkylating agent stream with a first alkylation catalyst having a first poison capacity in a first alkylation reaction zone under suitable at least partially liquid phase first reaction conditions to remove at least a portion of said impurities, and to alkylate a portion of said alkylatable aromatic compound with said first alkylating agent stream, and produce a first alkylated stream comprising alkylated aromatic compound(s) (e.g., mono-alkylated and polyalkylated aromatic compounds), unreacted alkylatable aromatic compound, any remaining water, and any remaining impurities, preferably, wherein said remaining impurities are reduced by at least 25% as compared to said impurities in said dehydrated stream; and (d) contacting said first alkylated stream and a second alkylating agent stream with a second alkylation catalyst different from said first alkylation catalyst, said second alkylation catalyst having a second poison capacity, in a second alkylation reaction zone under suitable at least partially liquid phase second reaction conditions to alkylate at least a portion of said unreacted alkylatable aromatic compound with said second alkylating agent stream and produce a second alkylated stream comprising additional said alkylated aromatic compound(s), unreacted alkylatable aromatic compound, any remaining water, and any remaining impurities.

In the reactive guard bed, a portion of the reactive impurities (e.g., catalyst poisons) which could otherwise poison the second alkylation catalyst are removed from the feed stream in the first alkylation reaction zone by the first alkylation catalyst at the same time as the alkylatable aromatic compound is alkylated with alkylating agent.

In operation of another embodiment (e.g., non-reactive guard bed), the process for producing alkylated aromatic compounds, for example mono-alkylated and poly-alkylated aromatic compounds, such process comprises the steps of: (a) supplying a feed stream to a dehydration zone, said feed stream comprising an alkylatable aromatic compound, water, and impurities, wherein said impurities comprise a compound having at least one of the following elements: nitrogen, halogens, oxygen, sulfur, arsenic, selenium, tellurium, phosphorus, and Group 1 through Group 12 metals; (b) removing at least a portion of said water from said feed stream in said dehydration zone to produce a dehydrated stream comprising said alkylatable aromatic compound, any remaining water, and said impurities; (c) contacting at least a portion of said dehydrated stream with a first catalyst having a first poison capacity in a first reaction zone under suitable at least partially liquid phase first reaction conditions to remove at least a portion of said impurities, and produce an alkylatable aromatic stream having a reduced amount of impurities comprising said alkylatable aromatic compound, any remaining water, and any remaining impurities, preferably, wherein said remaining impurities are reduced by at least 25% as compared to said impurities in said dehydrated stream; and (d) contacting said alkylatable aromatic stream and an alkylating agent stream with an alkylation catalyst different from said first catalyst, said alkylation catalyst having a second poison capacity, in an alkylation reaction zone under suitable at least partially liquid phase second reaction conditions to alkylate at least a portion of said unreacted alkylatable aromatic compound with said second alkylating agent stream and remove additional impurities to produce a second alkylated stream comprising alkylated aromatic compound(s), unreacted alkylatable aromatic compound, any remaining water, and any remaining impurities. After removing additional impurities in said first reaction zone, the amount of impurities in said first alkylated stream is 25% less, 20% less, 15% less, 10% less or 5% less based on the weight of said feed stream. Preferably, the amount of impurities in said first alkylated stream after removing additional impurities in said first reaction zone is less than 100 wppb, 75 wppb, 50 wppb or 25 wppb.

In the non-reactive guard bed, the impurities are removed from the feed stream in the first reaction zone by the first catalyst in the absence of the alkylating agent and there is no alkylation of the alkylatable aromatic compound.

Preferably at least 80%, or at least 70%, or at least 60%, or at least 50%, by weight, of said impurities are removed in step (c).

Optionally in step (b), at least a portion of said impurities in said feed stream are removed in said dehydration zone. Preferably, the impurities in said dehydrated stream after step (b) is 10% less, 5% less or 1% less by weight than the impurities in said feed stream. More preferably, the impurities in said dehydrated stream after removing at least a portion of impurities in the dehydration zone is less than 1000 wppb, less than 750 wppb, less than 500 wppb or less than 250 wppb.

In the reactive guard bed, the first poison capacity of said first alkylation catalyst may be greater than said second poison capacity of said second alkylation catalyst. Preferably, the first poison capacity of said first alkylation catalyst is at least 5%, at least 10%, at least 15%, at least 20%, at least 25%, at least 30%, at least 35%, at least 40%, at least 45% or at least 50% greater than said second poison capacity of said second alkylation catalyst.

In the non-reactive guard bed, the first poison capacity of said first catalyst may be greater than said second poison capacity of said alkylation catalyst. Preferably, the first poison capacity of said first catalyst is at least 5%, at least 10%, at least 15%, at least 20%, at least 25%, at least 30%, at least 35%, at least 40%, at least 45% or at least 50% greater than said second poison capacity of said alkylation catalyst.

In the reactive guard bed, the portion of said alkylated aromatic compound that is alkylated with alkylating agent in step (c) is at least 1%, at least 2%, at least 5%, at least 7%, at least 10%, at least 13% or at least 15% of said alkylatable aromatic compound.

In the reactive guard bed, the flow rate of said second alkylating agent stream may be greater than the flow rate of said first alkylating agent stream. Preferably, the flow rate of said second alkylating agent stream is at least 5%, at least 10%, at least 15%, at least 20%, at least 25%, at least 30%, at least 35%, at least 40%, at least 45% or at least 50% greater than the flow rate of said first alkylating agent stream.

In some embodiments, prior to step (c) said dehydrated stream is fed to a treatment zone containing a treatment material, and then said dehydrated stream is contacted with said treatment material in said treatment zone under suitable treatment conditions to remove at least a portion of said remaining amount of impurities and to produce a treated dehydrated stream. In these embodiments, the amount of impurities after contact with said treatment material is 1% less, 5% less, 10% less or 15% less by weight than is said dehydrated stream.

In some embodiments, prior to step (c) said dehydrated stream is fed to a treatment zone containing a treatment material, and then said dehydrated stream is contacted with said treatment material in said treatment zone under suitable treatment conditions to remove at least a portion of said remaining amount of impurities and to produce said first alkylated stream. In these embodiments, the amount of impurities after contact with said treatment material is 1% less, 5% less, 10% less or 15% less by weight than is said dehydrated stream.

In other embodiments, prior to step (a) said feed stream is fed to a treatment zone containing a treatment material, and then said feed stream is contacted with said treatment material in said treatment zone under suitable treatment conditions to remove at least a portion of said impurities. Preferably, the amount of impurities after treatment is 1% less, 5% less, 10% less or 15% less by weight than is said feed stream. In these embodiments, the treatment material is selected from the group consisting of clay, resin, activated alumina, Linde type X, Linde type A and combinations thereof.

In the reactive guard bed, said first alkylation catalyst is a large pore molecular sieve having a Constraint Index of less than 2. Such large pore molecular sieve is selected from the group of consisting of zeolite beta, faujasite, zeolite Y, Ultrastable Y (USY), Dealuminized Y (Deal Y), Rare Earth Y (REY), Ultrahydrophobic Y (UHP-Y), mordenite, TEA-mordenite, ZSM-3, ZSM-4, ZSM-14, ZSM-18, ZSM-20 and combinations thereof.

In the non-reactive guard bed, said first catalyst is a large pore molecular sieve having a Constraint Index of less than 2. Such large pore molecular sieve is selected from the group of consisting of zeolite beta, faujasite, zeolite Y, Ultrastable Y (USY), Dealuminized Y (Deal Y), Rare Earth Y (REY), Ultrahydrophobic Y (UHP-Y), mordenite, TEA-mordenite, ZSM-3, ZSM-4, ZSM-14, ZSM-18, ZSM-20 and combinations thereof.

The second alkylation catalyst (e.g., reactive guard bed) or the alkylation catalyst (e.g., non-reactive guard bed) is a MCM-22 family material having unit cells of MWW framework topology and characterized by an X-ray diffraction pattern including d-spacing maxima at $12.4\pm0.25$, $3.57\pm0.07$ and $3.42\pm0.07$ Angstroms. Such MCM-22 family material is selected from the group consisting of ERB-1, ITQ-1, ITQ-2, ITQ-30, PSH-3, SSZ-25, MCM-22, MCM-36, MCM-49, MCM-56, UZM-8, EMM-10, EMM-10P, EMM-12, EMM-13 and mixtures thereof.

After removing at least a portion of water in the dehydration zone, the water in said dehydrated stream is less than 100 wppm, less than 50 wppm, less than 25 wppm or less than 10 wppm based on said dehydrated stream.

The water is removed, for example, via distillation, adsorption, evaporation, extraction or flashing. The dehydration zone is a distillation column, a benzene column or a lights column.

After removing additional impurities in said first alkylation zone or said first reaction zone, the amount of impurities in said first alkylated stream is 25% less, 20% less, 15% less, 10% less or 5% less based on the weight of said feed stream. Preferably, the amount of impurities in said first alkylated stream after removing additional impurities in said first alkylation zone is less than 100 wppb, 75 wppb, 50 wppb or 25 wppb.

The impurities in said second alkylated stream is 10% less, 5% less or 1% less by weight than the impurities in said first alkylated stream. Preferably, the impurities in said second alkylated stream is less than 1 wppm, less than 5 wppm, less than 10 wppm, less than 15 wppm, less than 20 wppm or less than 25 wppm.

In some embodiments, the alkylation reaction zone(s) are preferably located in a single reactor vessel. Alternatively, said first alkylation reaction zone may be located in a separate vessel and may operate as a reactive guard bed. Said first reaction zone may be located in a separate vessel and may operate as a non-reactive guard bed. The catalyst in the reactive or non-reactive guard bed is subject to more frequent regeneration and/or replacement than the second alkylation catalyst, and hence it is typically provided with a by-pass circuit so that the alkylation feed(s) may be fed directly to the series connected reaction zones in the reactor while the guard bed is out of service.

Preferably the by-passable reactive guard bed is located upstream from the second alkylation zone. The by-passable non-reactive guard bed is located upstream from the alkylation zone. Such guard beds may be operated in co-current upflow or downflow operation. The reactive or non-reactive guard bed is maintained under suitable at least partial liquid phase conditions.

In the reactive guard bed, at least a portion of the alkylatable aromatic compound and at least a portion of the alkylating agent are passed through the reactive guard bed prior to entry into the second alkylation reaction zone.

In the non-reactive guard bed, the alkylatable aromatic compound is passed through the non-reactive guard bed prior to entry into the alkylation reaction zone.

The catalyst composition used in the reactive guard bed or the non-reactive guard bed is different from the catalyst composition used in the second and subsequent alkylation reaction zone(s). The catalyst composition used in the reactive guard bed or the non-reactive guard bed may have multiple catalyst compositions (e.g., a mixture of mordenite and zeolite Y, or a mixture of zeolite beta and zeolite Y). The reactive guard bed and normally each alkylation reaction zone, is maintained under conditions effective to cause alkylation of the alkylatable aromatic compound with the alkylating agent in the presence of an alkylation.

In other embodiments, said dehydrated stream further comprises at least a portion of an overhead stream from a distillation zone.

In another embodiment, said dehydrated stream is cooled to condense at least a portion of said dehydrated stream to remove at least a portion of any remaining water and impurities.

In another embodiment, the process further comprises the step of supplying said dehydrated stream to a distillation zone to remove said at least a portion of any remaining water before contacting step (c).

In another embodiment, the process further comprises the step of combining said dehydrated stream with a stream from a distillation zone to remove at least a portion of any said remaining water before contacting step (c), said distillation zone is a distillation column, a benzene column or a lights column.

The process of Claim 1, further comprising the step of supplying as reflux to a distillation column at least a portion of said dehydrated stream from said dehydration zone.

In some embodiments, said alkylatable aromatic compound is benzene. Said first alkylating agent stream or said second alkylating agent stream comprises an olefin. Optionally, said first or second alkylating agent stream comprises only alkylating agent and impurities, or only alkylating agent and water, or a mixture of alkylating agent and impurities and water.

Said alkylated aromatic compound is a mono-alkylated aromatic compound in some embodiments. In such case, said alkylating agent is ethylene and said mono-alkylated aromatic compound is ethylbenzene, or said alkylating agent is propylene and said mono-alkylated aromatic compound is cumene, or said alkylating agent is butylene, and said mono-alkylated aromatic compound is sec-butyl benzene.

In some embodiments of the process, a mono-alkylated aromatic compound stream, and optionally said poly-alkylated compound stream, is separated from said second alkylated stream.

Said alkylated aromatic compound is a poly-alkylated aromatic compound, wherein the process further comprises the step of contacting said poly-alkylated aromatic compound of step (e) with a transalkylation catalyst in a transalkylation reaction zone under suitable transalkylation conditions to produce an additional amount of said mono-alkylated aromatic compound.

In another embodiment, said transalkylation catalyst is a large pore molecular sieve having a Constraint Index of less than 2.

In another embodiment, said large pore molecular sieve is selected from the group of consisting of zeolite beta, faujasite, zeolite Y, Ultrastable Y (USY), Dealuminized Y (Deal Y), Rare Earth Y, mordenite, TEA-mordenite, ZSM-3, ZSM-4, ZSM-18, ZSM-20 and combinations thereof.

The alkylation reactor used in the process of the present disclosure may be highly selective to the desired mono-alkylated aromatic compound, such as ethylbenzene, but typically produces at least some poly-alkylated species. The effluent from the final alkylation reaction zone may be subjected to a separation step to recover mono-alkylated and polyalkylated aromatic compounds. At least a portion of the poly-alkylated aromatic compound may be supplied to a transalkylation reactor which may be separate from the alkylation reactor. In the transalkylation reactor, the poly-alkylated aromatic compound is reacted with the alkylatable aromatic compound to produce an effluent which contains additional mono-alkylated aromatic compound. At least a portion of these effluents may be separated to recover the alkylated aromatic compound (mono-alkylated aromatic compound and/or poly-alkylated aromatic compound).

One or more embodiments of this disclosure are illustrated in FIGS. 1 to 8.

Figure 1:
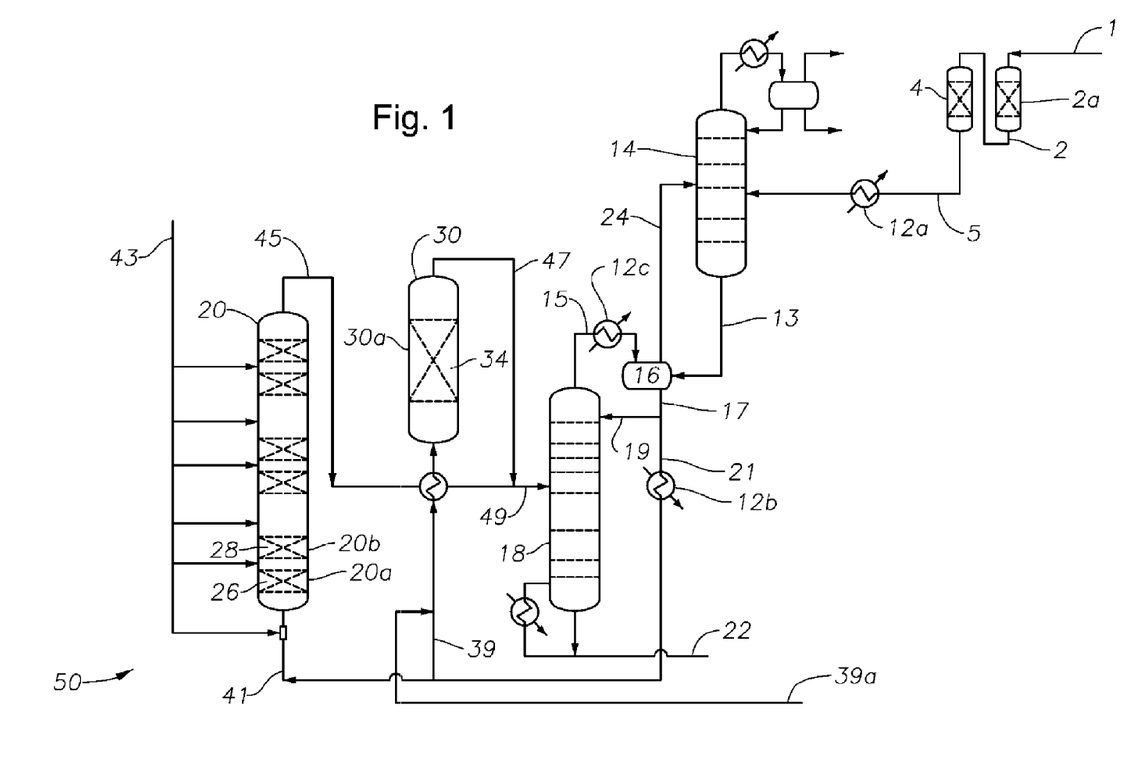
FIGS. 1-8 are each process flow diagrams of a process for producing alkylated aromatic compounds in accordance with an embodiment of the present disclosure.

FIG. 1 shows a process 50 for producing an alkylated aromatic compound, for example, a mono-alkylated aromatic compound, such as ethylbenzene, in which a feed stream 1, comprising an alkylatable aromatic compound, water and impurities, is fed to treaters 2 having a treatment zone 2*a* containing a treatment material 4 where it is treated under suitable treatment conditions to remove a first portion of said impurities, referenced above, and to produce a treater effluent stream 5. Optionally, the treater effluent stream 5 may be heated or cooled in heat exchanger 12*a*.

The treater effluent stream 5 is then fed to a dehydration zone 14, such as a lights removal distillation column, whereat least a portion of said water, and optionally a second portion of said impurities are removed from treater effluent stream 5 to produce a dehydrated stream 13 comprising said alkylatable aromatic compound, any remaining amount of water and said impurities.

The dehydrated stream 13 is fed to accumulator 16 of distillation zone 18. Distillation zone 18 may be a benzene distillation column. In accumulator 16, dehydrated stream 13 is combined with the overhead stream 15 from distillation zone 18 (which is cooled by a heat exchanger 12c) to produce an accumulator effluent 17. A portion of accumulator effluent 17 is fed as reflux 19 to distillation zone 18. Vapors 24 from accumulator 16 are fed to dehydration zone 14 for further separation. Stream 21, the remaining portion of accumulator effluent 17, forms an alkylatable aromatic feed stream 41 to alkylator 20 and an alkylatable aromatic feed stream 39 to transalkylator 30. Optionally, stream 21 may be heated or cooled in heat exchanger 12b. Heavier compounds (e.g., poly-alkylated aromatic compounds) are removed as a bottoms stream 22 of distillation zone 18 and separated in downstream separation equipment (not shown) to produce a mono-alkylated aromatic compound, such as ethylbenzene and polyalkylated aromatic compounds, such as polyalkylated feed stream 39a, discussed below.

Alkylator 20 has at least a first alkylation zone 20a which contains a first alkylation catalyst 26 located upstream of and in fluid communication with at least a second alkylation zone 20b which contains a second alkylation catalyst 28. In some embodiments, there is a plurality of series-connected alkylation zones. The first alkylation catalyst has a first poison capacity and the second alkylation catalyst has a second poison capacity, wherein the first poison capacity is greater than the second poison capacity. In this embodiment, the first alkylation reaction zone is a reactive guard bed that is integral within alkylator 20.

The first alkylation catalyst 26 comprises a large pore molecular sieve having a Constraint Index of less than 2. In some embodiments, the second alkylation catalyst comprises a MCM-22 family molecular sieve, referenced above. In other embodiments, the second alkylation catalyst comprises a medium pore molecular sieve having a Constraint Index of 2-12.

In the first alkylation zone 20a, the alkylatable aromatic feed stream 41 to the alkylator and a portion of first alkylating agent stream 43 are contacted with the first alkylation catalyst 26 in the first alkylation reaction zone under suitable at least partially liquid phase first reaction conditions. At least a portion, by weight, of said impurities are removed, and at least a portion, by weight, of said alkylatable aromatic compound is alkylated with said first alkylating agent stream 43, to produce a first alkylated stream comprising alkylated aromatic compound(s), unreacted alkylatable aromatic compound, any remaining water and any remaining impurities.

The first alkylated stream is contacted with another portion of said alkylating agent 43 in the presence of a second alkylation catalyst 28 (different from said first alkylation catalyst) in a second alkylation reaction zone 20b under suitable at least partially liquid phase second reaction conditions. Said unreacted alkylatable aromatic compound is alkylated with said second alkylating agent stream, to produce a second alkylated stream comprising additional said alkylated aromatic compound(s), any remaining water and any remaining impurities. The first and second alkylated streams, and subsequent alkylation zones, if any, combine to form an alkylated effluent 45 comprising unreacted alkylatable aromatic compound, any remaining water and mono-alkylated and poly-alkylated aromatic compounds. Unlikely, but possible there is some residual alkylation agent present.

The alkylatable aromatic feed stream 39 to the transalkylator, comprising the alkylatable aromatic compound, and the polyalkylated feed stream 39a (comprising the poly-alkylated aromatic compound from the downstream separation equipment (not shown)), are fed to transalkylation zone 30a of transalkylator 30. Transalkylation zone 30a has at least one transalkylation catalyst 34. In some embodiments, the transalkylation catalyst 34 is a large pore molecular sieve having a Constraint Index of less than 2.

In transalkylation zone 30a, the poly-alkylated aromatic compound in the polyalkylated feed stream 39a is contacted with the transalkylator alkylatable aromatic feed stream 39 in the presence of transalkylation catalyst 34 under suitable at least partially liquid phase transalkylation conditions, to produce additional said mono-alkylated aromatic compound in transalkylator effluent 47.

The alkylated effluent 45, optionally combined with transalkylator effluent 47, are fed as distillation feed stream 49 to distillation zone 18, to separate the mono-alkylated compounds from said poly-alkylated compounds and heavier compounds.

Figure 2:
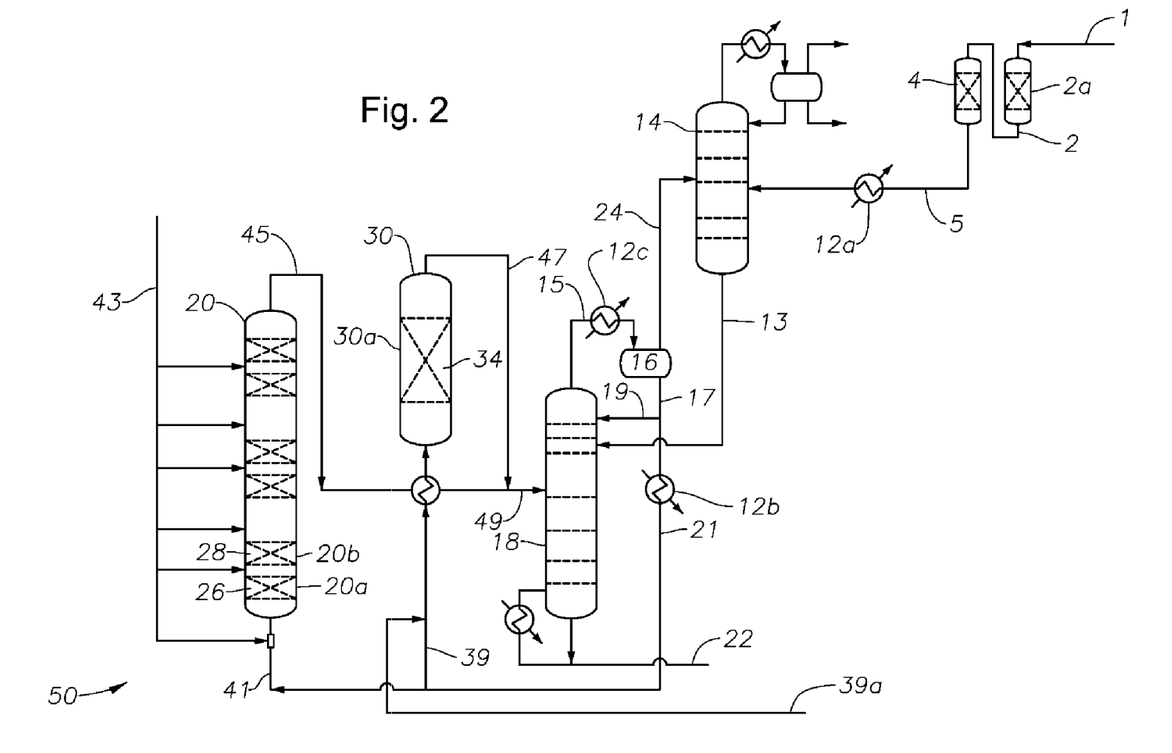
Figure 3:
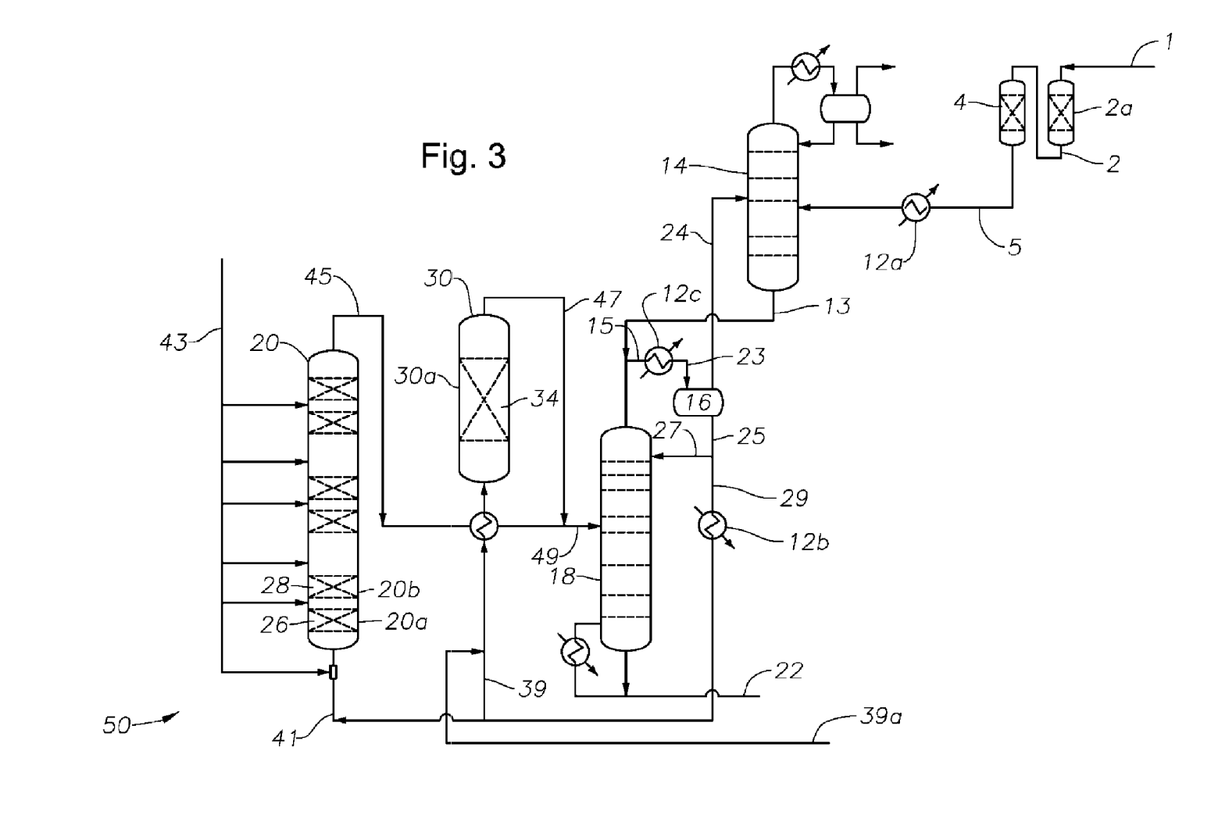
Figure 4:
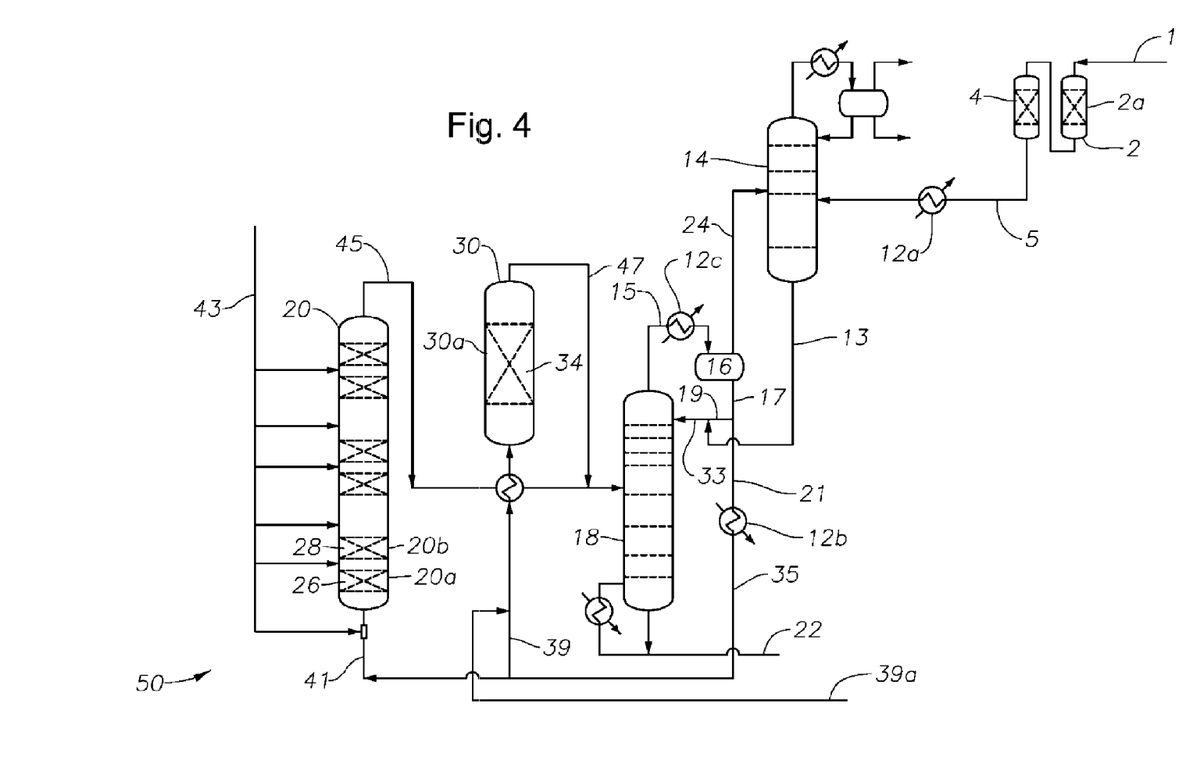

FIGS. 2-4 show alternative embodiments of the use of dehydrated stream 13 in the distillation zone 18 of process 50 for producing a mono-alkylated aromatic compound of FIG. 1. The pieces of equipment and streams with the same numerals as in FIG. 1 are the same. In the embodiment of FIG. 2, the dehydrated stream 13, along with reflux 19, are fed to the distillation zone 18. Overhead stream 15 is cooled in heat exchanger 12c and then flows into accumulator 16. Stream 17, which comprises the alkylatable aromatic stream, flows from accumulator 16. A portion of stream 17 is split off and feed as the reflux 19, referenced above, to distillation zone 18. As in FIG. 1, stream 21, the remaining portion of stream 17, forms the transalkyator alkylatable aromatic feed stream 39 to transalkylator 30, and the alkylatable aromatic feed stream 41 to alkylator 20.

In the embodiment of FIG. 3, the dehydrated stream 13 is combined with the overhead stream 15 from distillation zone 18 and then cooled in heat exchanger 12c to form stream 23 which is then fed to accumulator 16. Stream 25, comprising the alkylatable aromatic compound, flows from accumulator 16 and is split into reflux stream 27 and stream 29. Stream 29, the remaining portion of stream 25, forms the transalkyator alkylatable aromatic feed stream 39 to transalkylator 30, and the alkylatable aromatic feed stream 41 to alkylator 20.

In the embodiment of FIG. 4, the overhead stream 15 of distillation zone 18 flows into accumulator 16 to form stream 17 as in FIG. 1. In this embodiment, the dehydrated stream 13 is combined with reflux stream 19 to form combined reflux stream 33 to distillation zone 18. Stream 35, the remaining portion of stream 17, forms the transalkyator alkylatable aromatic feed stream 39 to transalkylator 30, and the alkylatable aromatic feed stream 41 to alkylator 20. Optionally, stream 35 may be heated or cooled in a heat exchanger 12b.

Figure 5:
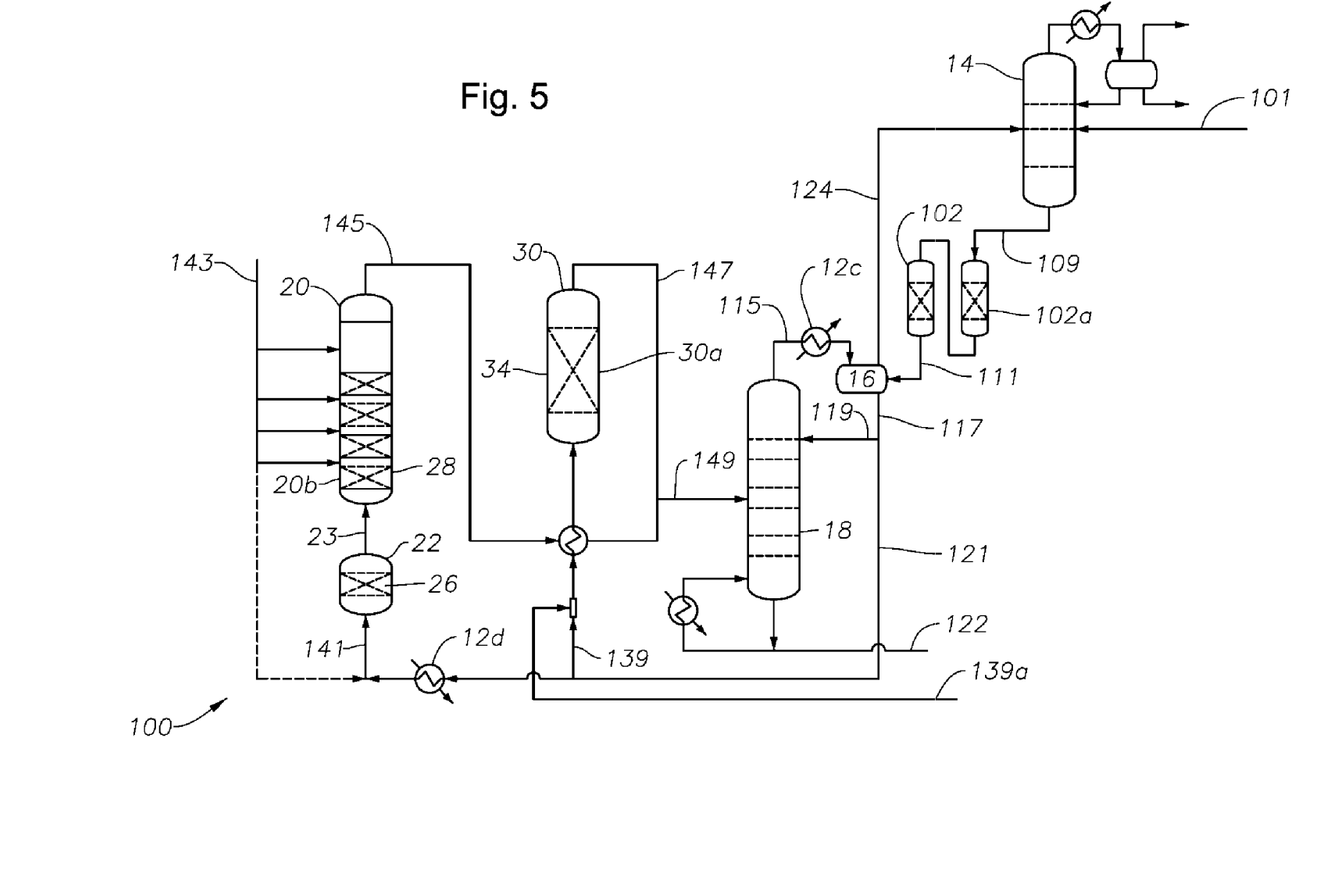

FIG. 5 shows a process 100 for producing a mono-alkylated aromatic compound 100, such as ethylbenzene, using a guard bed in a separate vessel, and which is operated in a reactive mode or a non-reactive mode. When the guard bed is operated in non-reactive mode, no alkylating agent is fed. When the guard bed is operated in reactive mode, it receives a portion of an alkylation agent.

Feed stream 101, comprising an alkylatable aromatic compound, water and impurities are fed to dehydration zone 14, such as a lights removal distillation column. The pieces of equipment and streams with the same numerals as in FIG. 1 are the same. In dehydration zone 14, at least a portion of said water, and optionally a portion of said impurities are removed from the feed stream 101 to produce a dehydrated stream 109 comprising said alkylatable aromatic compound, any remaining amount of said impurities and any remaining water. The dehydrated stream 109 is fed to a treatment zone 102 containing a treatment material 102a where it is treated under suitable treatment conditions to remove additional said impurities and to produce effluent stream 111. The impurities and treatment material 102a are the same as those described above. Optionally, the effluent stream 111 may be heated or cooled in a heat exchanger (not shown).

Effluent stream 111 is fed to accumulator 16 of distillation zone 18, where it is combined with the overhead stream 115 from distillation zone 18 to produce a combined effluent 117. Distillation zone 18 may be a benzene distillation column. A portion of combined effluent 117 is fed as reflux 119 to distillation zone 18. Vapors 124 from accumulator 16 are fed to dehydration zone 14 for further separation. Stream 121, the remaining portion of combined effluent 117, may be heated or cooled in a heat exchanger 12d. Also, stream 121 forms an alkylatable aromatic feed stream 139 to transalkylator 30, and an alkylatable aromatic feed stream 141 to (reactive or non-reactive) guard bed 22. Heavier compounds (e.g., poly-alkylated aromatic compounds) are removed as a bottoms stream 122 of distillation zone 18 and separated in downstream separation equipment (not shown) to produce an alkylated aromatic compound, such as ethylbenzene, and polyalkylated aromatic compounds, such as polyalkylated feed stream 139a, discussed below.

Guard bed 22 is separate from alkylator 20 and located upstream of and is in fluid communication with at least a second alkylation zone 20b. When guard bed 22 is a reactive guard bed, it is the first alkylation zone and contains a first alkylation catalyst 26. When guard bed 22 is a non-reactive guard bed, is not an alkylation zone because no alkylating agent is fed.

Second alkylation zone 20b contains a second alkylation catalyst 28. The first alkylation catalyst has a first poison capacity and is different from the second alkylation catalyst which has a second poison capacity. The first poison capacity is greater than the second poison capacity. Preferably, the first alkylation catalyst 26 comprises a large pore molecular sieve having a Constraint Index of less than 2.

In some embodiments, the second alkylation catalyst comprises a MCM-22 family molecular sieve, referenced above. In other embodiments, the second alkylation catalyst comprises a medium pore molecular sieve having a Constraint Index of 2-12.

When guard bed 22 is a reactive guard bed, the alkylatable aromatic feed stream 141 and a portion of alkylating agent stream 143 are contacted in the presence of the first alkylation catalyst 26, under at least partial liquid phase condition, to form the first alkylated stream which comprises comprising alkylated aromatic compound(s), unreacted alkylatable aromatic compound, any remaining water and any remaining impurities.

When guard bed 22 is a non-reactive guard bed, it receives the alkylatable aromatic feed stream 141 which is contacted with the first alkylation catalyst 26 (in the absence of alkylating agent) under suitable at least partially liquid phase first reaction conditions to remove at least a portion, by weight, of said impurities, and produce an alkylatable aromatic stream comprising said alkylatable aromatic compound, any remaining water and any remaining impurities.

The first alkylated stream or the alkylatable aromatic stream is then fed to second alkylation zone 20b and contacted with additional alkylating agent stream 143 in the presence of second alkylation catalyst 28, under suitable at least partially liquid phase second reaction conditions, to produce a second alkylated stream which comprises additional amounts of alkylated aromatic compounds.

The first and second alkylated streams, and subsequent alkylation zones, if any, combine to form an alkylated effluent 145 comprising an alkylated aromatic compound, unreacted alkylatable aromatic compound, any remaining water and any remaining impurities.

The transalkylator alkylatable aromatic feed stream 139, comprising the alkylatable aromatic compound, and poly-alkylated aromatic feed stream 139a, comprising the poly-alkylated aromatic compound, are fed to transalkylation zone 30a. Transalkylation zone 30a has at least one transalkylation catalyst 34. In some embodiments, transalkylation catalyst 34 is a large pore molecular sieve having a Constraint Index of less than 2.

In transalkylation zone 30a, the poly-alkylated aromatic feed stream 139a is contacted with transakylator alkylatable aromatic feed stream 139 in the presence of transalkylation catalyst 34 under suitable at least partially liquid phase transalkylation conditions to produce additional said mono-alkylated aromatic compound in transalkylator effluent 147.

The alkylated effluent 145, optionally combined with transalkylator effluent 147, are fed as distillation feed stream 149 to distillation zone 18, to separate the mono-alkylated compounds from said poly-alkylated compounds and heavier compounds. The polyalkylated and heavier compounds are separated in downstream separation equipment (not shown).

Figure 6:
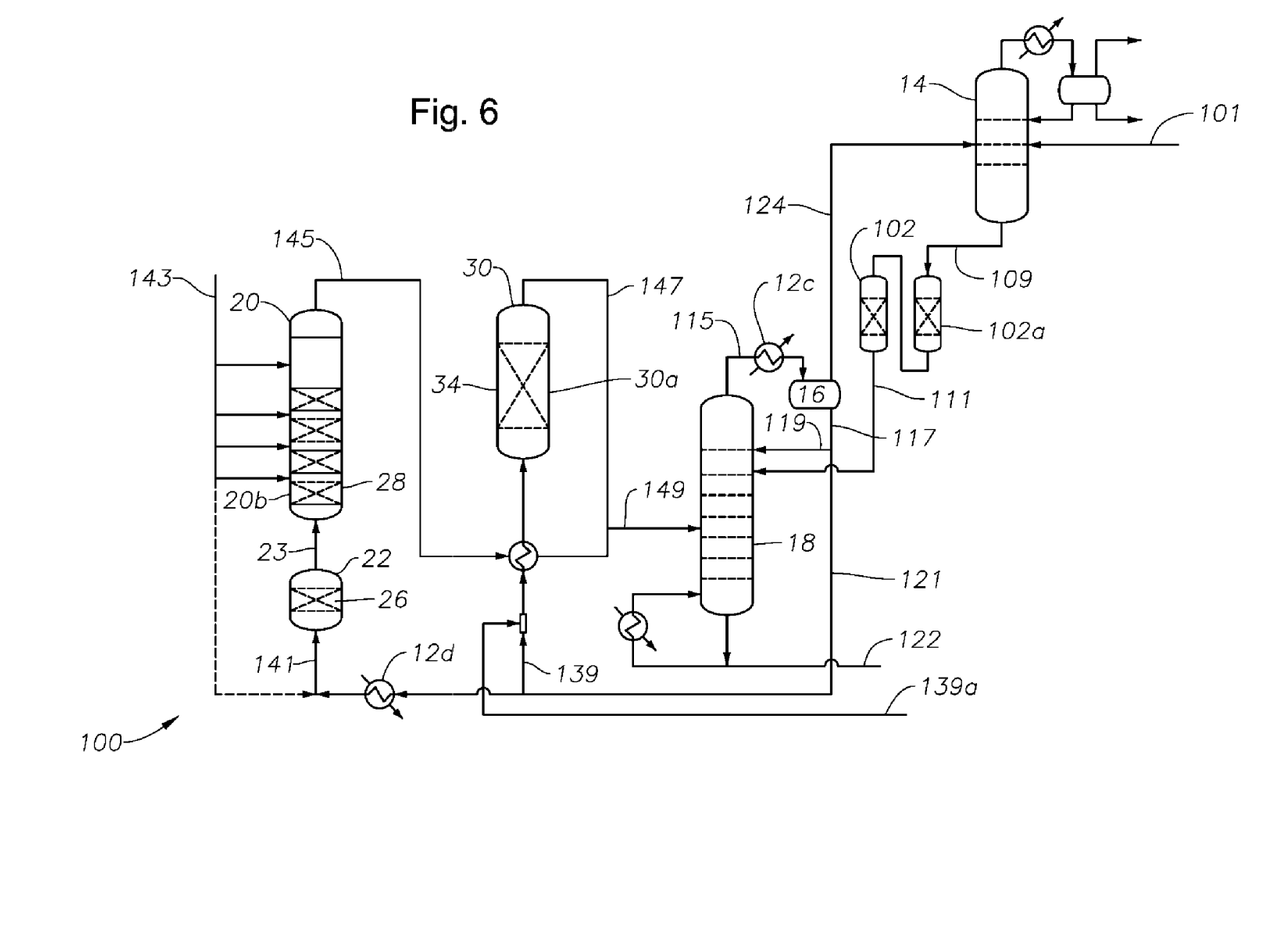
Figure 7:
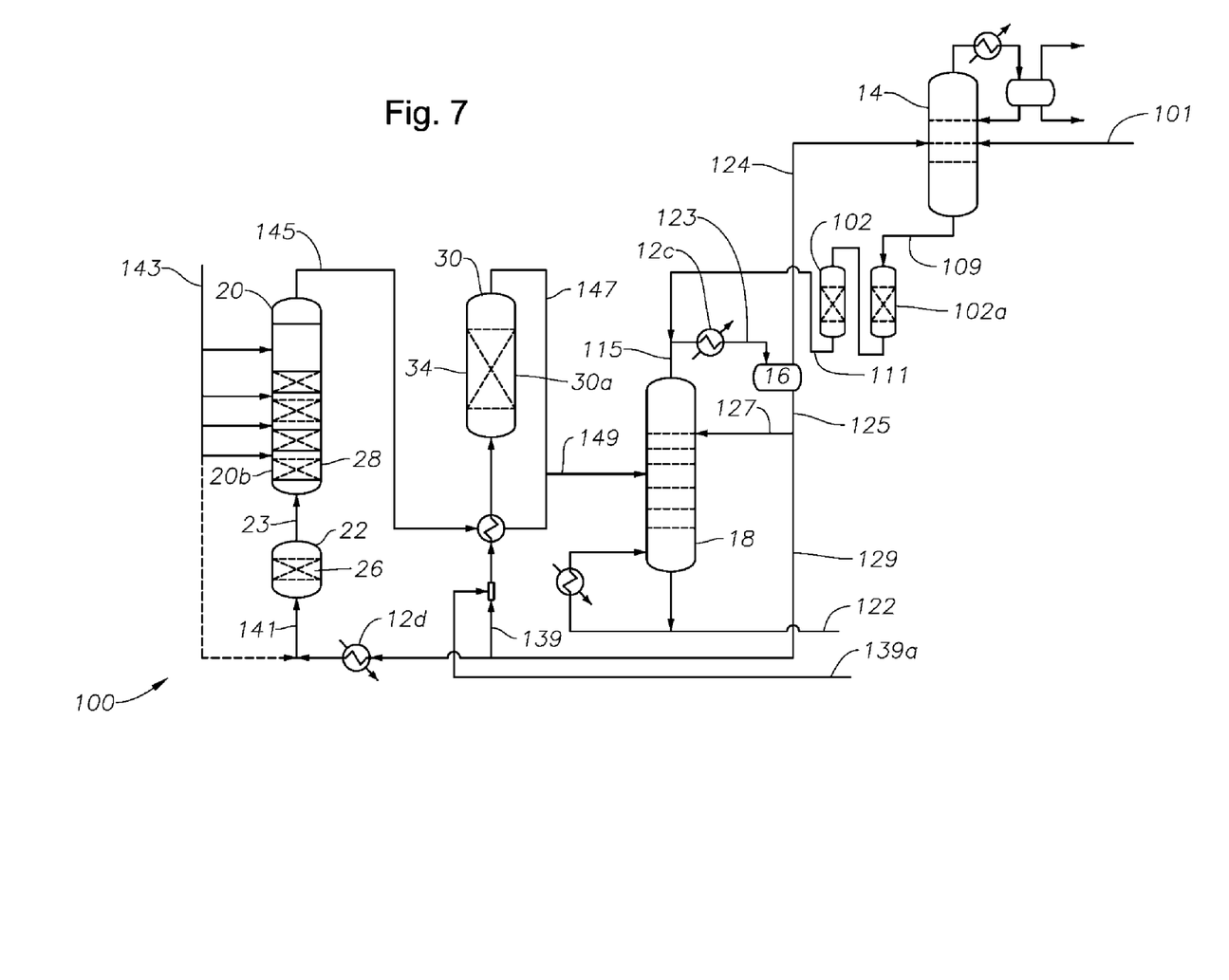
Figure 8:
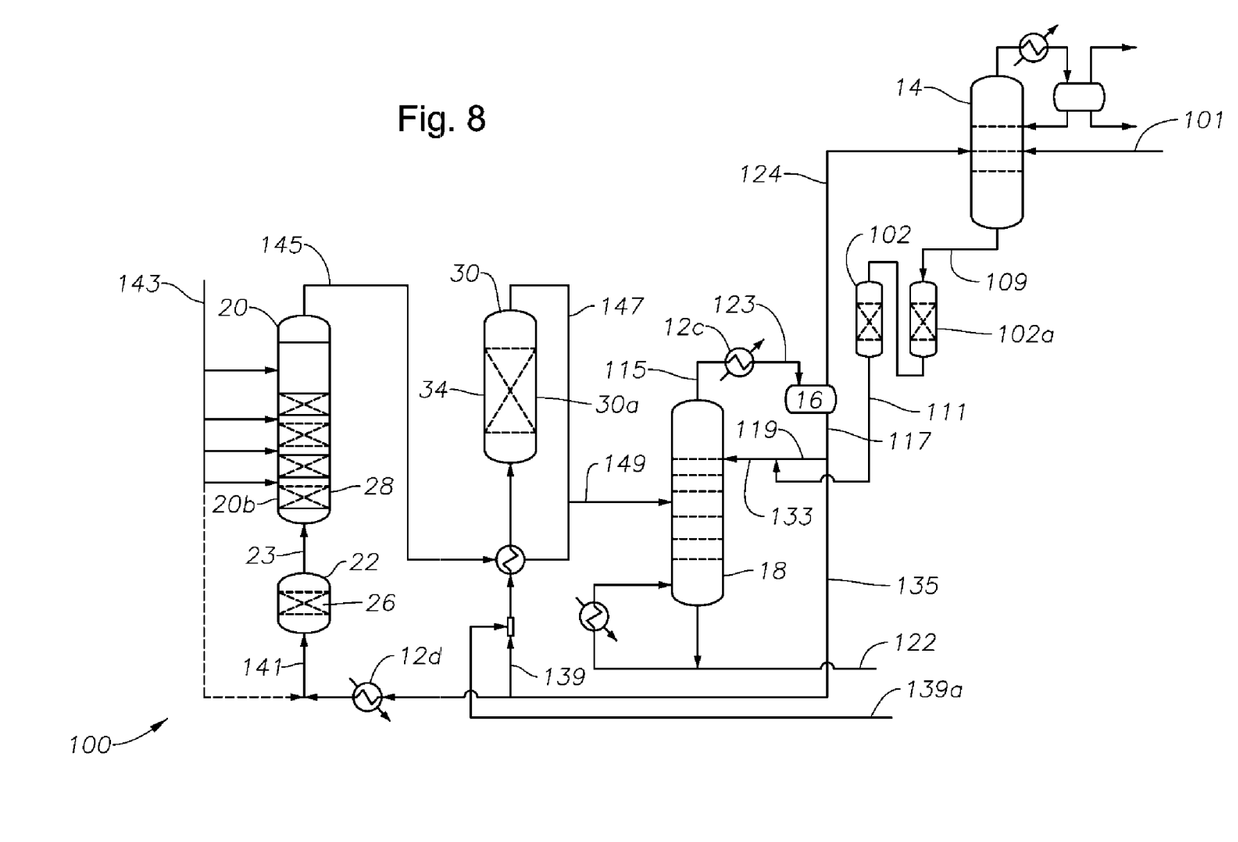

FIGS. 6-8 show alternative embodiments of the use of effluent stream 111 (which comprises dehydrated stream 109) in distillation zone 18 of process 100 for producing a mono-alkylated aromatic compound of FIG. 5. The pieces of equipment and streams with the same numerals as in FIG. 5 are the same. In the embodiment of FIG. 6, the effluent stream 111 along with reflux stream 119 is fed to the distillation zone 18. Overhead stream 115 of distillation zone 18 flows into accumulator 16. Stream 117, which comprises the alkylatable aromatic stream, flows from accumulator 16. A portion of stream 117 is split off and fed as reflux 19 to distillation zone 18. Stream 121, the remaining portion of stream 117, forms the transalkylator feed stream 139 to transalkylator 30, and the alkylator feed stream 141 to guard bed 22, as in FIG. 5. Optionally, stream 121 may be heated or cooled in heat exchanger 12d.

In the embodiment of FIG. 7, the effluent stream 111 is combined with the overhead stream 115 from distillation zone 18 and then cooled in heat exchanger 12c to form stream 123 which is then fed to accumulator 16. Stream 125, comprising the alkylated aromatic compound, flows from accumulator 16. This stream 16 is split into reflux stream 127 and stream 129. Stream 129, the remaining portion of stream 125, forms the transalkylator alkylatable aromatic feed stream 139 to transalkylator 30, and the alkylatable aromatic feed stream 141 to guard bed 22. Optionally, stream 129 may be heated or cooled in a heat exchanger 12d.

In the embodiment of FIG. 8, the overhead stream 115 flows into accumulator 16 to form stream 117 and reflux stream 119 as in FIG. 5. In this embodiment, the effluent stream 111 is combined with stream 119 that is split off of stream 17 to form reflux stream 133 to distillation zone 18. Stream 135, the remaining portion of stream 117, forms the transalkylator alkylatable aromatic feed stream 139 to transalkylator 30, and the alkylatable aromatic feed stream 141 to guard bed 22. Optionally, stream 135 may be heated or cooled in a heat exchanger 12d.

The disclosure will now be more particularly described with reference to the following Examples.

Examples 1-6

Measurement of Poison Capacity

In Examples 1-6, the poison capacity for collidine was determined by feeding collidine in the gas phase in which its uptake was recorded via thermogravimetric analyzer. The total uptake is one measure of a zeolite's capacity for adsorbing nitrogen-containing compounds.

TABLE 1

| Example | Catalyst | Zeolite Content (%) | Approximate Poison Capacity (meq/g) |
|---|---|---|---|
| 1 (Comparative) | MWW (MCM-49) | 80 | 80-130 |
| 2 | Beta (Non-MWW) | 80 | 701 |
| 3 | USY (Non-MWW) | 80 | 925 |
| 4 | ZSM-12 (Non-MWW) | 65 | 531 |
| 5 | Mordenite (Non-MWW) | 65 | 385 |
| 6 | Solid Phosphoric Acid (Non-MWW) | None | 501 |

As can been seen, Table 1 shows that the poison capacity using collidine for a catalyst having MWW topology is much less than that for catalyst having non-MWW topology.

Examples 7 and 8

In Examples 7 and 8, the capacity of an MWW and zeolite beta catalysts to absorb an N-formyl morpholine (NFM) impurity was determined Two alkylation reactors were placed in series with an NFM impurity-containing benzene feed supplied to a first alkylation reactor having first alkylation catalyst (Rx 1). The effluent of Rx 1 was the feed to a second alkylation reactor having a second alkylation catalyst (Rx 2). Rx1 and Rx2 each reactor had a separate ethylene injection points and this configuration is like the first two stages of a multi-stage series-connected alkylation reactor. For these experiments Rx 1 was a reactive guard bed and was the first reaction zone in an alkylation reactor. Deactivation of Rx 2 was used to indicate when Rx 1 has achieved its maximum poison capacity and catalyst poisons were no longer completely retained by Rx 1. NFM was fed at a concentration of 0.3 wt wppm based on the weight of the benzene feed.

The NFM absorption capacities in the Examples are calculated from the time on stream and the time at which deactivation is observed in Rx 2.

TABLE 2

| Example | Zeolite for Rx1 (80 wt. % zeolite content based on weight of zeolite) | Zeolite for Rx2 (80 wt. % zeolite content based on weight of zeolite) | NFM Absorption Capacity (wppm based on the weight of the zeolite) |
|---|---|---|---|
| 7 (Comparative) | MWW | MWW | 900-1000 |
| 8 | Beta | MWW | 5950 |

As can been seen, Table 2 shows that the NFM absorption capacity for zeolite beta as the first catalyst is superior to a first catalyst comprising an MWW catalyst.

All patents, patent applications, test procedures, priority documents, articles, publications, manuals and other documents cited herein are fully incorporated by reference to the extent such disclosure is not inconsistent with this disclosure and for all jurisdictions in which such incorporation is permitted.

When numerical lower limits and numerical upper limits are listed herein, ranges from any lower limit to any upper limit are contemplated.

While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

We claim:

1. A process for producing an alkylated aromatic compound, said process comprising the steps of:
   (a) supplying a feed stream to a dehydration zone, said feed stream comprising an alkylatable aromatic compound, water and impurities, wherein said impurities comprise a compound having nitrogen as an element;
   (b) removing at least a portion of said water from said feed stream in said dehydration zone operated under suitable dehydration conditions to produce a dehydrated stream comprising said alkylatable aromatic compound, any remaining water and said impurities;
   (c) feeding at least a portion of said dehydrated stream to a treatment zone containing a treatment material;
   (d) contacting said portion of said dehydrated stream with said treatment material in said treatment zone under suitable treatment conditions to remove at least a portion of said impurities, wherein said treatment material is selected from the group consisting of clay, resin, activated alumina, Linde type X, Linde type A and combinations thereof;
   (e) contacting at least a portion of said dehydrated stream from step (d) with a first catalyst having a first poison capacity in a guard bed of a first reaction zone under suitable at least partially liquid phase first reaction conditions to remove at least a portion of said impurities, and produce an alkylatable aromatic stream having a reduced amount of impurities and comprising said alkylatable aromatic compound, any remaining water, and any remaining impurities, wherein said first catalyst is a large pore molecular sieve selected from the group of consisting of zeolite beta, faujasite, zeolite Y, Ultrastable Y (USY), Dealuminized Y (Deal Y), Rare Earth Y (REY), Ultrahydrophobic Y (UHP-Y), mordenite, TEA-mordenite, ZSM-3, ZSM-4, ZSM-14, ZSM-18, ZSM-20 and combinations thereof; and
   (f) contacting a portion of said alkylatable aromatic stream from step (e) and an alkylating agent stream with an alkylation catalyst different from said first catalyst, said alkylation catalyst having a second poison capacity greater than said first poison capacity, in an alkylation reaction zone under suitable at least partially liquid phase second reaction conditions to alkylate at least a portion of said alkylatable aromatic stream with said alkylating agent stream and produce an alkylated stream comprising alkylated aromatic compound(s), unreacted alkylatable aromatic compound, any remaining water, and any remaining impurities, wherein said alkylation catalyst is a MCM-22 family material selected from the group consisting of ERB-1, ITQ-1, ITQ-2, ITQ-30, PSH-3, SSZ-25, MCM-22, MCM-36, MCM-49, MCM-56, UZM-8, EMM-10, EMM-10P, EMM-12, EMM-13 and mixtures thereof.

2. The process of claim 1, wherein in removing step (b) at least a portion of said impurities in said feed stream are removed in said dehydration zone.

3. The process of claim 1, wherein prior to contacting step (a) said feed stream is fed to a treatment zone containing a treatment material, and then said feed stream is contacted with said treatment material in said treatment zone under suitable treatment conditions to remove at least a portion of said impurities.

4. The process of claim 3, wherein said treatment material is selected from the group consisting of clay, resin, activated alumina, Linde type X, Linde type A and combinations thereof.

5. The process of claim 1, wherein said first reaction zone is in a separate vessel from said alkylation reaction zone.

6. The process of claim 1, wherein said first reaction zone is in the same vessel as said alkylation reaction zone.

7. The process of claim 1, further comprising the step before feeding step (c) of combining said dehydrated stream from step (b) with a stream from a distillation zone to remove said remaining water before feeding step (c).

8. The process of claim 1, further comprising the step before feeding step (c) of supplying said dehydrated stream from step (b) to a distillation zone to remove said any remaining water before feeding step (c), said distillation zone is a distillation column, a benzene column or a lights column.

9. The process of claim 1, wherein said dehydrated stream from step (b) further comprises at least a portion of an overhead stream from a distillation zone.

10. The process of claim 1, further comprising the step of supplying at least a portion of said dehydrated stream from step (b) as reflux to a distillation column.

11. The process of claim 1, wherein said dehydrated stream from step (b) is cooled to condense at least a portion of said dehydrated stream to remove at least a portion of said any remaining water and impurities.

12. The process of claim 1, wherein said alkylatable aromatic compound is benzene.

13. The process of claim 1, wherein said alkylating agent stream comprises an olefin and said impurities, and wherein at least a portion of said impurities are removed in contacting step (f).

14. The process of claim 1, wherein said alkylating agent is ethylene and said mono-alkylated aromatic compound is ethylbenzene, or said alkylating agent is propylene and said mono-alkylated aromatic compound is cumene, or said alkylating agent is butylene and said mono-alkylated aromatic compound is sec-butyl benzene.

15. The process of claim 1, wherein said alkylated aromatic compound(s) of said alkylated stream comprises mono-alkylated aromatic compounds and poly-alkylated aromatic compounds.

16. The process of claim 15, wherein said process further comprising the step of:
(e) separating a mono-alkylated aromatic compound stream from said alkylated stream.

17. The process of claim 15, further comprising the step of:
(f) separating a poly-alkylated aromatic compound stream from said alkylated stream.

18. The process of claim 17, further comprising the step of:
(g) contacting said poly-alkylated aromatic compound stream and another portion of said alkylatable aromatic stream with a transalkylation catalyst in a transalkylation reaction zone under suitable at least partially liquid phase transalkylation conditions to transalkylate said poly-alkylated aromatic compound stream and produce additional said mono-alkylated aromatic compound.

19. The process of claim 18, wherein said transalkylation catalyst is a large pore molecular sieve having a Constraint Index of less than 2.

20. The process of claim 19, wherein said large pore molecular sieve is selected from the group of consisting of zeolite beta, faujasite, zeolite Y, Ultrastable Y (USY), Dealuminized Y (DealY), Rare Earth Y(REY), Ultrahydrophobic Y (UHP-Y), mordenite, TEA-mordenite, ZSM-3, ZSM-4, ZSM-14, ZSM-18, ZSM-20 and combinations thereof.

* * * * *